(12) United States Patent
Kvarnström et al.

(10) Patent No.: US 6,312,259 B1
(45) Date of Patent: Nov. 6, 2001

(54) BONE IMPLANT

(75) Inventors: Bjarne Kvarnström, Huntington Beach, VA (US); Michael Luft, Dover; Scott Lipka, Peru, both of IL (US)

(73) Assignee: Nobel Biocare AB (SE)

( * ) Notice: Subject to any disclaimer, the term of this patent is extended or adjusted under 35 U.S.C. 154(b) by 0 days.

(21) Appl. No.: 09/466,061

(22) Filed: Dec. 17, 1999

(51) Int. Cl.[7] .............................. A61C 8/00; A61C 3/00
(52) U.S. Cl. ..................... 433/173; 433/24; 433/174
(58) Field of Search ........................... 433/173, 174, 433/175, 172, 20.1, 2, 24

(56) References Cited

U.S. PATENT DOCUMENTS

| | | | |
|---|---|---|---|
| 4,511,336 | * | 4/1985 | Hidaka et al. ................... 433/173 |
| 5,092,771 | * | 3/1992 | Tatum, III ......................... 433/173 |
| 5,169,309 | * | 12/1992 | Staubli et al. ................... 433/173 |
| 5,697,779 | * | 12/1997 | Sachdeva et al. ............... 433/173 |
| 5,762,499 | * | 6/1998 | Dard et al. ....................... 433/173 |
| 5,769,630 | * | 6/1998 | Hoffman .......................... 433/173 |
| 5,836,768 | | 11/1998 | Hüskens et al. ................. 433/173 |
| 5,921,774 | * | 7/1999 | Kanomi et al. .................. 433/173 |

* cited by examiner

Primary Examiner—John J. Wilson

(57) ABSTRACT

An implant for providing an anchor in bone tissue. A retention portion for implanting into the bone tissue includes at least one retention member for retaining the implant in a preprepared hole in the bone tissue and includes an insertion end. An abutment portion extends from the retention portion opposite the insertion end and has a larger diameter than the retention portion. The abutment portion is for passing through soft tissue one the bone tissue. A stop portion extends from the abutment portion for contacting a member attached to the implant. An attachment groove includes an attachment surface for attaching at least one member connected to another structure. A top portion has a diameter greater than the attachment groove.

24 Claims, 3 Drawing Sheets

BONE IMPLANT

FIELD OF THE INVENTION

The present invention relates to an implant for being anchored in a hole formed in bone.

BACKGROUND OF THE INVENTION

In certain situations, it may be desirable to alter the position of skeletal elements, including teeth, of patients. The position of certain aspects of a skeleton in undesired locations can result from birth defects, injuries, or other actions. Frequently, perception of misplacement of skeletal elements results from vanity. In other words, cosmetic surgery can include movement of skeletal and/or dental elements.

To move a bone, portion of a bone, tooth, or other portion of a patient's body often requires application of force to the body portion to be moved over a period of time. For example, there may be a tendency for a skeletal part or tooth, for example, to move back to its original location. Also, it may mot be desired or possible to move a skeletal or dental part quickly. For example, repositioning of teeth in orthodontic applications typically requires a long period of time.

SUMMARY OF THE INVENTION

In view of the above, the present invention provides an implant for providing an anchor in bone tissue. A retention portion for implanting into the bone tissue includes at least one retention member for retaining the implant in a preprepared hole in the bone tissue. The retention portion includes an insertion end. An abutment portion extends from the retention portion opposite the insertion end and has a larger diameter than the retention portion. The abutment portion is for passing through soft tissue on the bone tissue. A stop portion extends from the abutment portion for contacting a member attached to the implant. An attachment groove includes an attachment surface for attaching at least one member connected to another structure. A top portion has a diameter greater than the attachment groove.

Still other objects and advantages of the present invention will become readily apparent by those skilled in the art from the following detailed description, wherein it is shown and described only the preferred embodiments of the invention, simply by way of illustration of the best mode contemplated of carrying out the invention. As will be realized, the invention is capable of other and different embodiments, and its several details are capable of modifications in various obvious respects, without departing from the invention. Accordingly, the drawings and description are to be regarded as illustrative in nature and not as restrictive.

BRIEF DESCRIPTION OF THE DRAWINGS

The above-mentioned objects and advantages of the present invention will be more clearly understood when considered in conjunction with the accompanying drawings, in which.

DETAILED DESCRIPTION OF THE INVENTION

As described above, it is often necessary or desirable to reposition elements of a patient's skeleton, including teeth or other structures in the mouth. Often, the repositioning includes application of force over a period of time to the element to be repositioned. The element typically resists the repositioning, and tends to remain or return to its original position.

The present invention provides an implant for anchoring in a hole in bone and for providing a structure that can serve as a point for application of force to the skeletal or dental element to be repositioned. The present invention is especially useful in orthodontic applications. However, the present invention may find usefulness in other applications as well.

Figure 1:
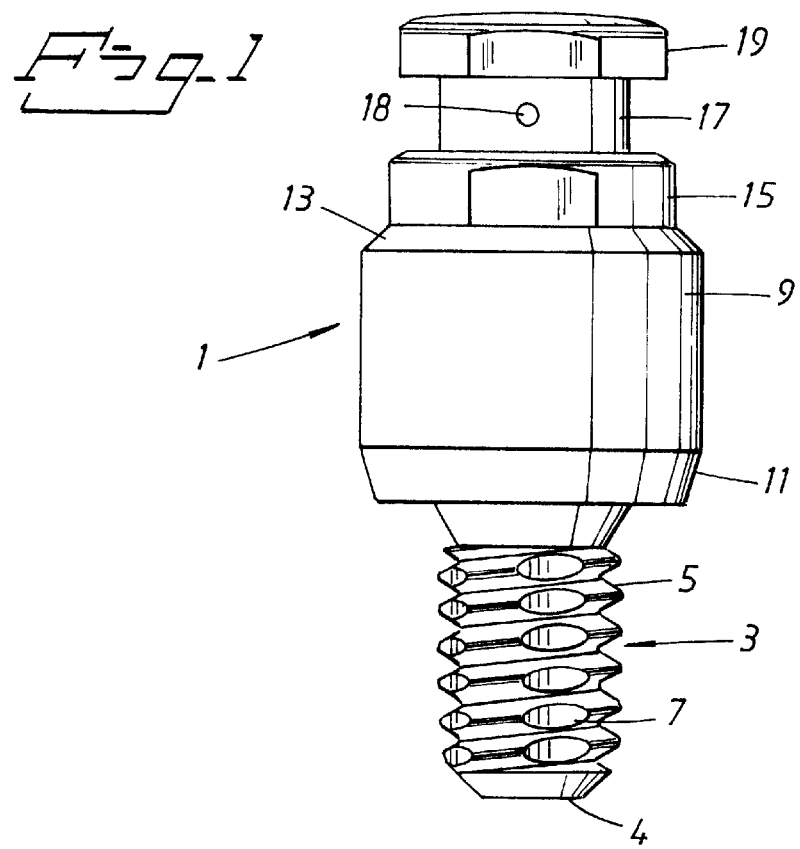
FIG. 1 represents a side view of an implant according to one embodiment of the present invention.
Figure 2:
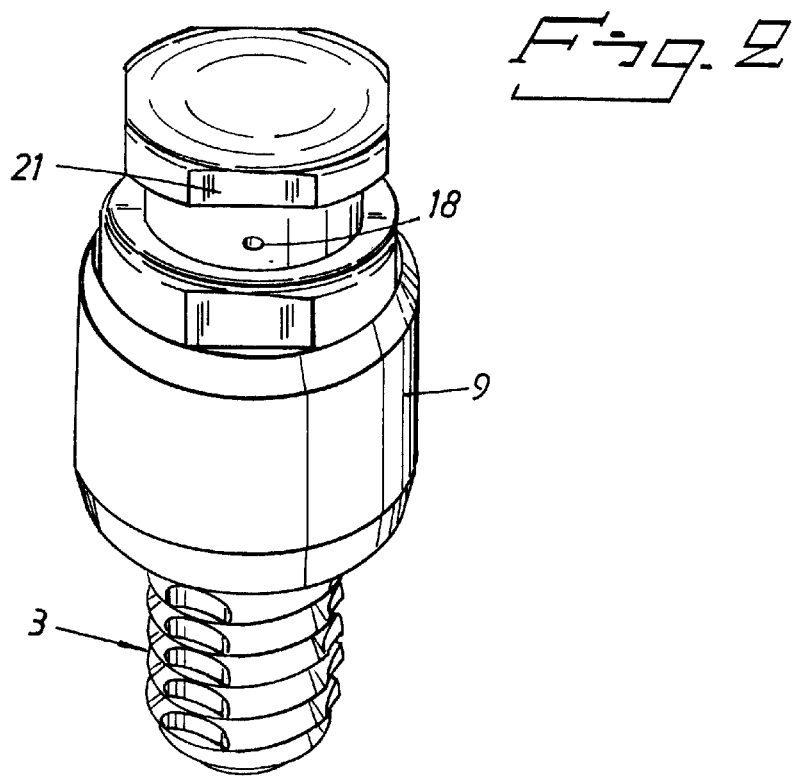
FIG. 2 represents a perspective view of the embodiment illustrated in FIG. 1.
Figure 3:
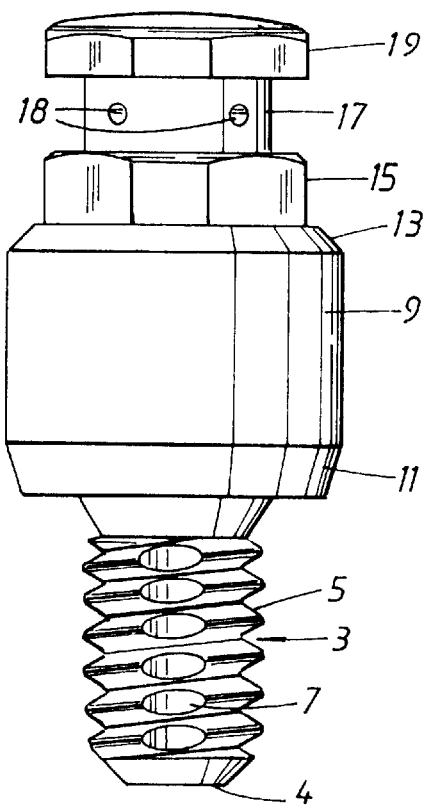
FIG. 3 represents another side view of the embodiment illustrated in FIGS. 1 and 2.
Figure 4:
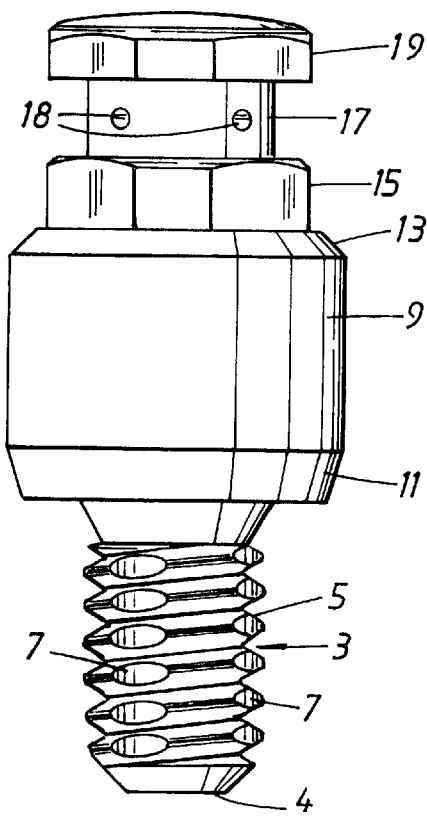
FIG. 4 represents a further side view of the embodiment illustrated in FIGS. 1–3.

FIG. 1 illustrates one example of an embodiment of an implant 1 according to the present invention. An implant according to the present invention includes a retention portion 3 for implanting into bone tissue. Accordingly, the present invention is actually implanted into a hole formed in bone tissue. The retention portion helps to lock the implant into the bone and helps to prevent the implant from coming loose under a load that could be applied to the implant during repositioning of one or more skeletal or dental structures.

Typically, the retention portion has a cylindrical cross-section. However, the retention portion may have any desired cross-sectional shape. Also, the retention portion may have any desired length and diameter. The specific application of an implant according to the invention may serve as one factor in determining the length and diameter of the retention part. Along these lines, the amount of space available for the implant and the amount of force that is to be applied to the skeletal or dental part to be moved may be factors that are considered in determining the length and diameter of the retention portion of an implant according to the present invention.

An insertion end 4 of the retention portion is first inserted into a hole in bone tissue. The retention portion of an implant according to the present invention includes at least one retention member for retaining the implant in a preprepared hole in bone tissue. The at least one retention member could include a threaded portion 5 such as the embodiment illustrated in FIG. 1. Other embodiments of the present invention could include a plurality of grooves and ridges having a shape similar to a thread, such as the thread illustrated in FIG. 1. However, such grooves and ridges are parallel to each other. On the other hand, a thread actually includes only a single continuous groove and ridge.

Other embodiments of an implant according to the present invention can include other retention elements in addition to or in place of a threaded portion or grooves. Along these lines, the retention portion can include a blasted or embossed surface. Such surfaces are not smooth and can serve to help to retain the implant in bone tissue through friction, as the threads or grooves described above.

Whether the retention portion includes grooves, a threaded portion, a contoured surface and/or other structures, the surface typically has qualities that result in osseointegration of the implant. Typically, such surfaces include small bumps, various contours, other surface features, and/or passages in and/or through the implant that help to retain the implant in the bone as the bone grows to fill in any spaces between the implant and the bone tissue. Those of ordinary skill in the art could determine the nature of a surface or other features that will result in osseointegration of an implant according to the present invention.

The retention portion of an implant according to the present invention may also include at least one antirotational feature to help prevent rotation of the implant in the bone tissue. The anti-rotational feature can include semi-lunar grooves 7, as in the embodiment shown in FIGS. 1–4. Typically, the at least one anti-rotational feature may be arranged on all or a portion of the retention portion of the implant. In some embodiments, the at least one anti-rotational feature may be arranged in the vicinity of the insertion end of the implant.

Extending from the retention portion, an implant according to the present invention may include an abutment portion, or trans-epithelial cuff. Along these lines, the embodiment illustrated in FIG. 1 includes abutment portion 9. The abutment portion 9 is for extending through soft tissue overlying bone tissue when the implant is installed in a patient. In a dental application, the abutment portion may extend through gingival tissue. The abutment portion helps to provide a seal with the tissue it extends through to help prevent any organisms or substances from migrating to the underlying bone. As such, the abutment portion can help to prevent infection and/or other problems associated with anything entering the passage that the implant is inserted into.

Typically, the abutment portion has a diameter wider than the retention portion. Similar to the retention portion, the abutment portion typically has a cylindrical cross-section. However, the abutment portion may have any other desired cross-sectional shape. The abutment portion could be conically shaped, tapering away from the retention portion.

Also, the abutment portion may have any desired length and diameter. As with the retention portion, the abutment portion may may have any desired length and diameter. The specific application of an implant according to the invention may serve as one factor in determining the length and diameter of the abutment part. Along these lines, the amount of space available for the implant and thickness of the tissue that the abutment portion is to extend through may be factors that are considered in determining the length and diameter of the abutment portion of an implant according to the present invention.

As stated above, the abutment portion typically has a diameter greater than the retention portion. In having a diameter greater than the retention portion, the junction between the abutment portion and the retention portion may act as a stabilizing feature because the diameter is greater than the retention portion. The greater diameter of the abutment portion as compared to the retention portion may also act as a positive stop to prevent the implant from penetrating too deeply into the bone tissue.

In the vicinity of the junction of the abutment portion and the retention portion, the abutment portion may include a beveled portion 11, as in the embodiment shown in FIGS. 1–4. The beveled portion may facilitate insertion of the implant into the soft tissue.

Extending from the abutment portion opposite the retention portion may be a stop portion. The stop portion may serve as a stop or platform for a component or instrument attached, temporarily or permanently to the implant. The stop portion thus acts to prevent an instrument or component from sliding down the implant onto the abutment portion.

The stop portion may include a surface inclined toward the longitudinal axis of the implant. Along these lines, the stop portion may include a beveled surface 13 on the abutment portion opposite the retention portion as in the embodiment shown in FIGS. 1–4. The stop portion can alternatively include a surface perpendicular to the longitudinal axis of the implant.

The stop portion may also include an extended portion 15 have a reduced diameter as compared to the abutment portion. The extended portion may include at least antirotational feature for helping to prevent the rotation of a component or instrument attached to the implant. The at least one anti-rotational feature may include at least one planar surface on the stop portion.

An attachment groove may be extend from the stop portion or stop portion extension. The embodiment illustrated in FIGS. 1–4 includes attachment groove 17. The attachment groove can provide a structure on the implant for attachment of at least one member connected to another structure. For example, in a dental application, at least one wire, spring and/or rubber band may be attached to the attachment groove. In the dental context or other application, the at least one wire attached to one or more teeth or skeletal structure to be repositioned or to a structure attached to the at least one tooth or skeletal structure. Along these lines, in a dental application, the rubber band, spring or wire could be attached to a tooth or to a band or other member attached to a tooth.

As shown in FIGS. 1–4, the attachment groove has a reduced diameter with respect to the abutment portion. The attachment groove may also have a reduced diameter with respect to the stop portion and/or stop portion extension. The attachment groove may have any desired length or diameter as long as the diameter is less than the diameter of the abutment portion. One factor that may control the length of the attachment groove is the number of wires, springs, and/or rubber bands to be attached to the implant. More wires, springs, and/or rubber bands may require a longer attachment groove.

To facilitate retention of any wire, spring, rubber band and/or other securing structure attached to the implant, the attachment groove may include at least one retention feature. The at least one retention feature may include at least one hole or other anti-rotational geometry through the implant in the attachment groove, at least one planar surface, and/or other retention feature.

The embodiment illustrated in FIG. 1–4 includes a pair of passages 18 through the implant. If the implant includes such passages, the implant could include only one passage. Such passages could be formed through the implant in any desired configuration. According to one example, the passage(s) pass through the longitudinal axis of the implant and are perpendicular thereto.

Extending from the attachment groove opposite the stop portion or stop portion extension typically is a top portion. The embodiment depicted in FIGS. 1–4 includes top portion 19. Top portion 19 has a diameter greater than the diameter of attachment groove 17. The greater diameter of the top portion helps to retain any wire(s), spring(s) and/or rubber band(s) attached to the attachment groove. With this in mind, the top portion may have any desired diameter. The top portion may also have any desired length.

Another structure or tool may be attached to the implant over at least the top portion of the implant. The top portion may include at least one anti-rotational feature to help prevent rotation of another structure or tool attached to the implant. The anti-rotational feature may be provided on the exterior of the top portion. According to such embodiments, the at least one anti-rotational feature may include at least one planar surface on the side of the top portion. Along these lines, the embodiment shown in FIGS. 1–4 includes four planar surfaces 21 on the side of the top portion.

Alternatively or additionally, the at least anti-rotational feature may be internal to the implant. In such embodiments, the at least one anti-rotational feature may include a passage that extends into the implant from the surface of the implant. The at least one anti-rotational feature may extend into the implant a distance greater than the thickness of the top portion.

To provide anti-rotational capacity, the anti-rotational passage has a non-circular cross-sectional shape. Along these lines, the passage could have a hexagonal or square cross-sectional shape. Of course, the passage could have any cross-sectional shape that permits the passage to prevent rotation of a portion of a component inserted therein.

An implant according to the present invention typically is made of a biocompatible material. Along these lines, typically, an implant according to the present invention is made of titanium. Of course, an implant according to the present invention may be made of any desired suitable material.

Figure 5:
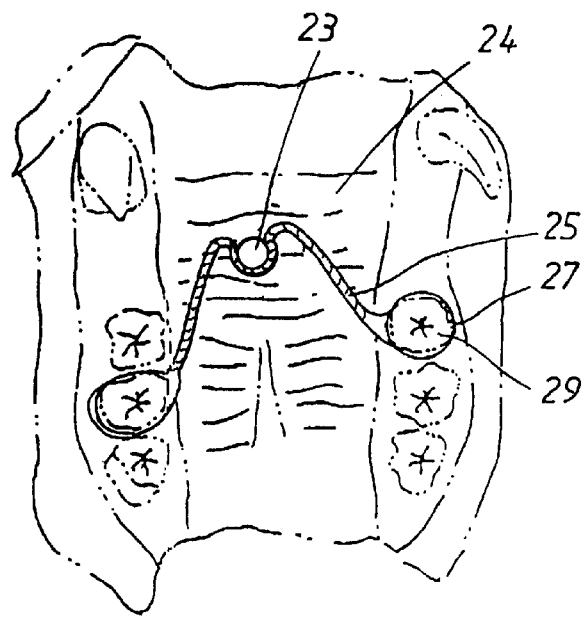
FIG. 5 represents one example of a dental application of an embodiment of an implant according to the present invention.
Figure 6:
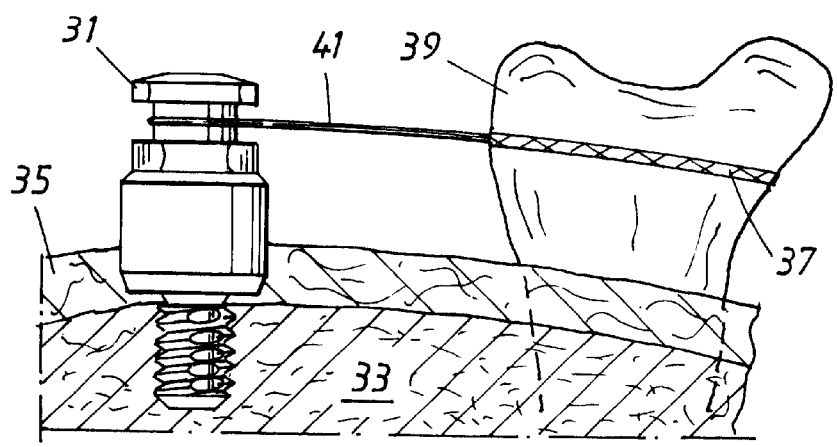
FIG. 6 represents a side partial cut-away view of another example of a dental application of an embodiment of an implant according to the present invention.

As stated above, the present invention is particularly useful in dental applications. FIGS. 5 and 6 illustrates two different examples of use of an implant according to the present invention in dental applications. Along these lines, FIG. 5 illustrates an implant 23 according to the present invention implanted into the soft palate 24 of the roof of a patient's mouth. The present invention may be utilized in animals and people.

In FIG. 5, two wires 25 are attached to the implant 23. Each wire 25 is attached to a band 27 attached to a tooth. In such an application, the implant according to the present invention could be utilized to apply force to the teeth 29 to alter the position of the teeth.

FIG. 6 illustrates an implant 31 according to the present invention implanted in a jawbone 33 of a patient. FIG. 6 illustrates the retention portion inserted into the bone tissue and the abutment portion extending through the soft tissue 35 overlying the bone tissue. In the application represented in FIG. 6, a band 37 has been attached to a tooth 39 whose position it to be altered. The band 37 has been interconnected to the implant 31 with a wire 41.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the is description is not intended to limit the invention to the form disclosed herein. Also, it is intended that the appended claims be construed to include alternative embodiments.

We claim:

1. An implant for providing an anchor in bone tissue, the implant comprising a retention portion for implanting into the bone tissue, the retention portion including at least one retention member for retaining the implant in a prepared hole in the bone tissue and including an insertion end; an abutment portion extending from the retention portion opposite the insertion end and having a larger diameter than the retention portion, the abutment portion for passing through soft tissue on the bone tissue; a stop portion extending from the abutment portion for contacting a member attached to the implant; an attachment groove for receiving at least one of rubber bands, wires, and springs, said groove having a reduced diameter with respect to said abutment portion and including an attachment surface for attaching at least one member connectable to another structure; a top portion having a diameter greater than the attachment groove; and at least one hole through the implant in the attachment groove.

2. The implant according to claim 1, wherein the at least one retention member comprises a screw thread.

3. The implant according to claim 1, wherein the at least one retention member comprises a plurality of retention grooves.

4. The implant according to claim 1, wherein the at least one retention member comprises a blasted or embossed surface.

5. The implant according to claim 1, further comprising:
at least one anti-rotational feature on the retention portion.

6. The implant according to claim 5, wherein the at least one anti-rotational feature is provided in the vicinity of the insertion end.

7. The implant according to claim 5, wherein the at least one anti-rotational feature comprises at least one semi-lunar groove.

8. The implant according to claim 1, wherein the abutment portion is capable of forming a seal with the soft tissue.

9. The implant according to claim 1, wherein the larger diameter of the abutment portion as compared to the retention portion acts as a stop to prevent penetration of the implant too deeply into the bone tissue.

10. The implant according to claim 1, wherein the stop portion comprises a beveled surface extending from the abutment portion.

11. The implant according to claim 1, wherein the stop portion comprises a shelf perpendicular to the longitudinal axis of the implant on the abutment portion.

12. The implant according to claim 1, wherein the rubber bands, wires or springs are attachable directly or indirectly to at least one tooth.

13. The implant according to claim 1, further comprising:
at least one anti-rotational feature on the groove.

14. The implant according to claim 13, wherein the attachment groove has a circular cross-section and the at least one anti-rotational feature comprises at least one flat surface on the groove.

15. The implant according to claim 13, wherein the at least one anti-rotational feature comprises at least one hole or surface for rotational lock of a wire and/or spring attached to the implant.

16. The implant according to claim 1, further comprising:
at least one ant-rotational feature on the top portion for preventing rotation of a component attached to the implant.

17. The implant according to claim 6, wherein the at least one anti-rotational feature comprises a plurality of flat surfaces on the top portion.

18. The implant according to claim 16, wherein the at least one anti-rotational feature is provided on an exterior surface of the top portion.

19. The implant according to claim 16, further comprising:
an internal passage in the implant, wherein the at least one anti-rotational feature is provided on a surface of the internal passage.

20. The implant according to claim 1, wherein the top portion prevents a wire, spring, or rubber band attached to the attachment groove from slipping off of the implant.

21. The implant according to claim 1, wherein the surface of the retention part permits osseointegration of the implant with the bone tissue.

22. The implant according to claim 1, wherein the other structure that the at least one attachment member is connectable to includes at least one tooth.

23. The implant according to claim 1, wherein the other structure that the at least one attachment member is connectable to includes a band attached to at least one tooth.

24. An implant for providing an anchor in bone tissue, the implant comprising a retention portion for implanting into the bone tissue, the retention portion including at least one retention member for retaining the implant in a prepared hole in the bone tissue and including an insertion end; an abutment portion extending from the retention portion opposite the insertion end and having a larger diameter than the retention portion, the abutment portion for passing through soft tissue on the bone tissue; a stop portion extending from the abutment portion for contacting a member attached to the implant; an attachment groove for receiving at least one of rubber bands, wires, and springs, said groove having a reduced diameter with respect to said abutment portion and including an attachment surface for attaching at least one member connectable to another structure; a top portion having a diameter greater than the attachment groove; at least one anti-rotational feature on the groove, and the attachment groove having a circular cross-section and the at least one anti-rotational feature comprising at least one flat surface on the groove.

* * * * *